United States Patent [19]

Liau et al.

[11] Patent Number: 5,766,949
[45] Date of Patent: Jun. 16, 1998

[54] METHOD AND APPARATUS FOR CULTIVATING ANCHORAGE DEPENDENT MONOLAYER CELLS

[75] Inventors: Ming-Yi Liau, No. 161, Kun-Yang St.; Ding-Yu Hsiun, both of Taipei City, Taiwan

[73] Assignee: Ming-Yi Liau, Taipei, Taiwan

[21] Appl. No.: 668,134

[22] Filed: Jun. 21, 1996

[51] Int. Cl.$^6$ .............................. C12M 3/04; C12M 3/02; C12M 1/36; C12M 1/16
[52] U.S. Cl. .................. 435/395; 435/286.5; 435/286.6; 435/289.1; 435/299.1
[58] Field of Search .................................. 435/293, 300, 435/301, 310, 286.6, 288.4, 288.5, 289.1, 290.4, 291.3, 395, 298.1, 299.1, 286.5

[56] References Cited

U.S. PATENT DOCUMENTS

| | | | |
|---|---|---|---|
| 4,080,258 | 3/1978 | McAleer et al. | 195/1.7 |
| 4,228,243 | 10/1980 | Iizuka | 435/285 |
| 5,240,854 | 8/1993 | Berry et al. | 435/284 |

OTHER PUBLICATIONS

Hu et al., "Animal Cell Bioreactors–Recent Advances and Challenges to Scale–Up" *The Canadian Journal of Chemical Engineering*, vol. 69, pp. 409–420 (Apr., 1991).
Freshney, R. Ian, *Culture of Animal Cells*, "Specialized Techniques", Chapter 23, pp. 371–377 (1994).

*Primary Examiner*—Lynette F. Smith
*Assistant Examiner*—Brett Nelson
*Attorney, Agent, or Firm*—Skjerven, Morrill, MacPherson, Franklin & Friel, LLP; Emily M. Haliday

[57] ABSTRACT

An apparatus for cultivating cells as disclosed includes a cell culture chamber having inlet and outlet ports, a substrate (7) with an anchorage surface for attachment of cells, and a system for circulating a culture medium in the cell culture chamber through the inlet and outlet ports. The medium circulating system cooperates with valves to control the surface level of the medium in order to submerge the anchorage surface in the culture medium and intermittently expose the substrate from the culture medium, thereby increasing the rate of gas exchange through a thin film of the culture medium formed on the anchorage surface. A method for cultivating cells by using the apparatus is also disclosed.

15 Claims, 2 Drawing Sheets

METHOD AND APPARATUS FOR CULTIVATING ANCHORAGE DEPENDENT MONOLAYER CELLS

BACKGROUND OF THE INVENTION

1. Field of the Invention

The invention relates to a method and apparatus for cultivating animal cells and particularly to a method and apparatus for cultivating anchorage dependent monolayer cells.

2. Description of the Prior Art

Owing to the increasing demand for animal cell derived products in pharmaceutical and biotechnology industries, the development of animal cell culture processes has been an indispensable task in the biomedical field. For most animal cell cultures such as mammalian cell cultures, substrates are necessary for anchoring the cells since the cells cannot grow in suspension in a culture medium. Many cell culture systems have been developed for cultivating anchorage-dependent animal cells. Examples of these systems include tissue culture flasks, roller bottles, cell factories, microcarriers in stirred tanks, hollow fibers and ceramic systems. (Wei-Shou Hu et al. "Animal Cell Bioreactors-Recent Advances and challenges to Scale-Up" *The Canadian Journal of Chemical Engineering,* "Specialized Techniques" Volume 69, April, 1991, pages 409-420; "Specialized Techniques," Culture of Animal Cells, Chapter 23, pages 371-377).

In animal cell culture processing, one of the basic requirements is to supply sufficient gas, such as oxygen, and nutrients. Insufficient supply of gas or nutrients will retard the growth of cells. Another requirement is to control the level of metabolic products which can inhibit cell growth when accumulated in the culture media in high concentration.

The roller bottle is a bath type system which has no medium circulating arrangement. The system includes bottles for receiving a culture medium and for rotating on a support. Typically, a cell culture medium is placed inside a rotating bottle in an amount of $\frac{1}{10}-\frac{1}{5}$ of the interior volume of the bottle, and cells are grown on the inner surface of the bottle. An increased amount of dissolved oxygen in the medium can be obtained because a thin film of the medium, which facilitates gas exchange between gas and liquid phases, is formed on the unsubmerged inner surface of the bottle during the rotation of the bottle. Therefore, sufficient gas or oxygen can be supplied to cells even when the cell density is high. This system also offer an increased surface area for cell attachment and gentle agitation. A transfusion device or a dispensing device such as a pipette or peristaltic pump can be used for adding fresh medium.

Nevertheless, the system is not available for pH and dissolved oxygen control. Moreover, due to the absence of a medium circulating arrangement, removal of toxic metabolic waste products and depletion of nutrients requires constant media changeover and is therefore labor-intensive. In large capacity production which requires a large number of roller bottles, it is laborious to operate the system and it is difficult to obtain a uniform quality product. Therefore, application of such roller bottles is limited.

Cell culture systems with culture medium circulating systems are advantageous for replenishment of the culture medium and removal of metabolites. In such systems, cells are constantly submerged in their culture media, and the rate of the culture media is controlled so as to supply sufficient nutrients and dissolved oxygen for cells.

Microcarrier systems are of circulation type which can be easily expanded for large capacity production. However, in addition to their expensive cost, handling of these systems is inconvenient owing to the easy separation of cells from microsubstrates, especially when high shear forces exist.

Another circulation type culture systems are plug flow bioreactors such as hollow fiber and ceramic systems. In hollow fiber systems, a medium passes through the lumen of fibers at a high flow rate and only a small fraction permeates through the fiber membrane. These hollow fiber systems generally provide high culture density or efficiency. Nevertheless, since the supply of small molecular weight nutrients and the removal of metabolites are generally achieved by molecular diffusion due to the concentration gradient across the membrane, dissolved oxygen and nutrients can be deficient as the length or thickness of the hollow fiber is increased. Therefore, the production of cells in large scale is still difficult with the hollow fiber systems.

In ceramic systems, cells are inoculated in the channels of a porous ceramic cylinder, and a medium is passed through the channels to provide nutrients and to remove the metabolites. The amount of dissolved oxygen is increased by using a pump which circulates the medium. However, in order to sufficiently supply dissolved oxygen, it is generally necessary to increase the rate of the medium circulation. The increase in the rate of the circulation can strip off the cells from their anchorage surfaces, thereby adversely affecting the production efficiency.

SUMMARY OF THE INVENTION

The primary object of the invention is to provide an animal cell cultivating system which includes a medium circulating system for ease of removal of metabolites and refreshment or replacement of culture medium and which permits a cell anchorage surface to emerge from the culture medium for ease of gas exchange between a thin film of medium and the gas whereby the problem of oxygen deficiency can be eliminated even for high density cells.

Another object of the invention is to provide an improved medium circulating system which does not produce high shear forces while permitting the medium to supply sufficient dissolved oxygen for the growth of cells.

Still another object of the invention is to provide an improved animal cell cultivating system which can be controlled and which can be easily designed for large scale production.

A further another object of the invention is to provide an improved animal cell cultivating system which has an increased surface area for attachment of cells and which can be easily operated for separation of cells from their cultivating substrates.

These and other objects can be achieved through the provision of an apparatus and method for cultivating anchorage-dependent cells in accordance with the present invention. Particularly, the apparatus of the invention comprises a cell culture chamber having inlet means, outlet means and substrate means having an anchorage surface for attachment of cells, and means for circulating a culture medium in the cell culture chamber through the inlet and outlet means. The apparatus further comprises means for submerging the anchorage surface in the culture medium when the culture medium is circulated, and means for intermittently exposing the substrate means from the culture medium when the culture medium is circulated so as to increase the rate of gas exchange through a thin film of the culture medium formed on the anchorage surface.

3

Preferably, the substrate means is stationary, and the submerging means and the exposing means cooperate with the circulating means to raise the surface level of the culture medium so as to submerge the substrate means and to lower the surface level of the culture medium in order to leave a thin film on the anchorage surface. Means for storing the culture medium is provided to be in fluid communication with the medium circulating means.

The submerging and exposing means may comprise control valves at the inlet and outlet means for controlling the inlet and outlet flow of the culture medium.

According to another aspect of the invention, a method for cultivating anchorage-dependent cells comprises:

(a) providing a cell culture chamber having an inlet, an outlet, and a substrate means with an anchorage surface for attachment of cells;

(b) circulating a culture medium in the cell culture chamber through the inlet and outlet of the culture chamber;

(c) submerging the anchorage surface in the culture medium when the culture medium is circulated; and (d) intermittently exposing the substrate means from the culture medium when the culture medium is circulated so as to increase the rate of gas exchange through a thin film of the culture medium formed on the anchorage surface after step (c)

Preferably, the anchorage surface is intermittently exposed by discharging the culture medium to lower the surface level of the culture medium so as to form a thin film of the culture medium on the anchorage surface. The anchorage surface is submerged by feeding the culture medium to raise the surface level of the culture medium to a height above the anchorage surface. The culture medium is continuously circulated from the commencement of cultivation until cells attach to the anchorage surface. After cells attach to the anchorage surface, the surface level of the culture medium is lowered and raised alternatingly so as to intermittently expose the anchorage surface of the substrate means at a predetermined time interval. The medium circulating operation with the constant changing of the surface level of the medium provides gentle agitation of the medium.

Other features and advantages of the present invention will become apparent in the following detailed description of the preferred embodiment, with reference to the accompanying drawings.

DETAILED DESCRIPTION OF THE PREFERRED EMBODIMENT

Figure 1:
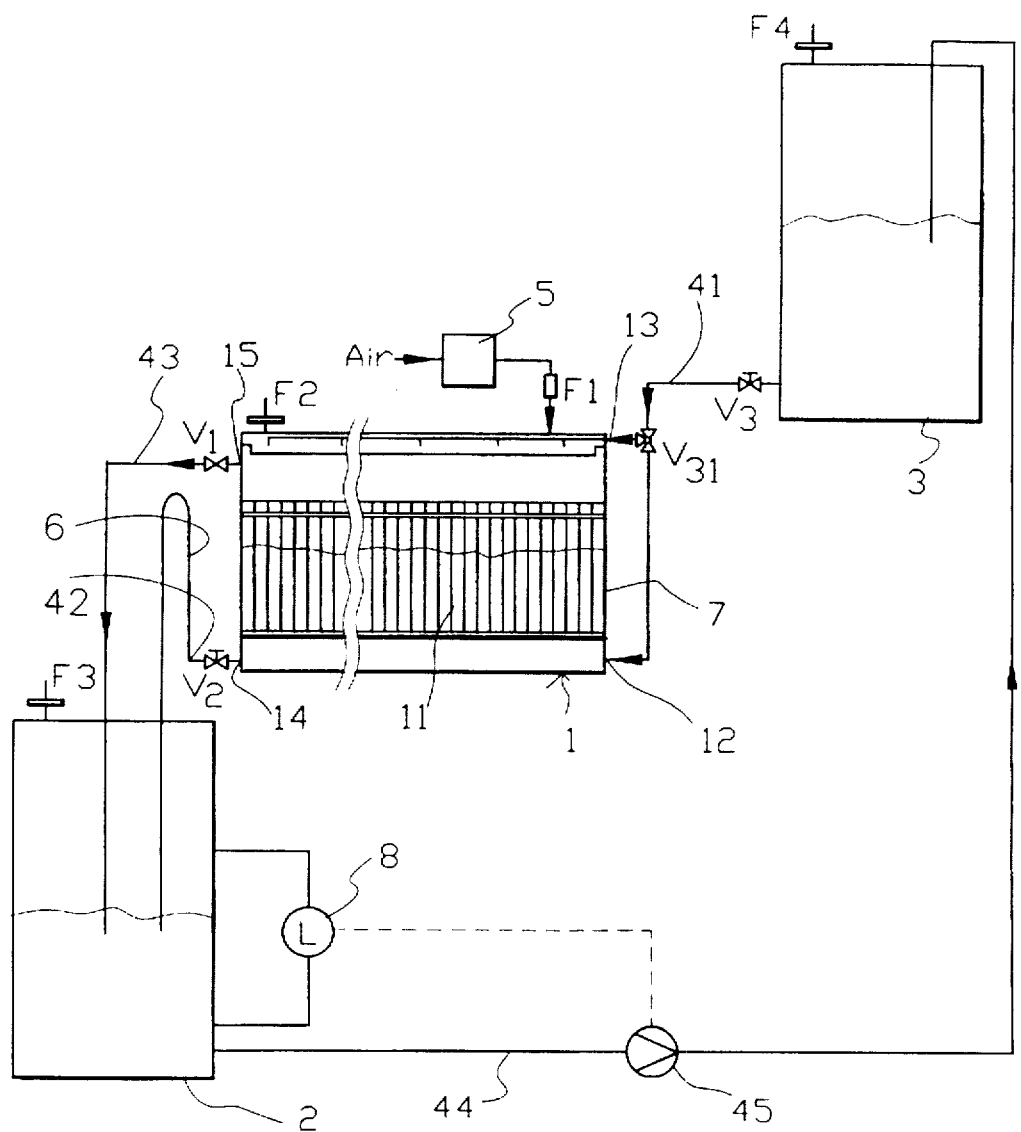
FIG. 1 is a schematic view showing a preferred embodiment of an apparatus for cultivating anchorage-dependent cells according to the present invention.
Figure 2:
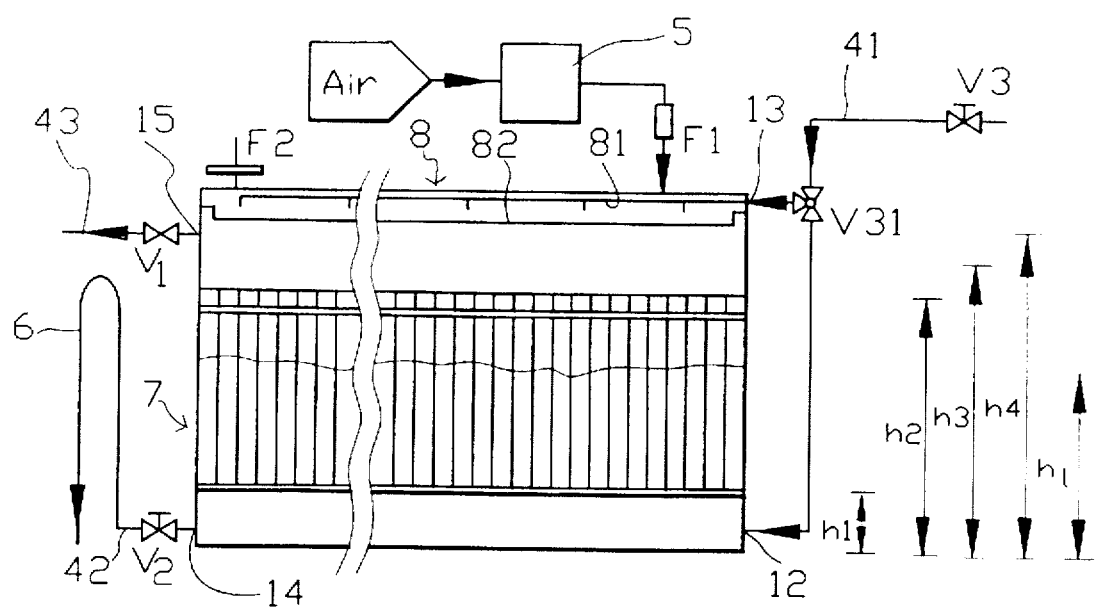
FIG. 2 is a view of a portion of the preferred embodiment, including the culture chamber shown in more detail.
Figure 3:
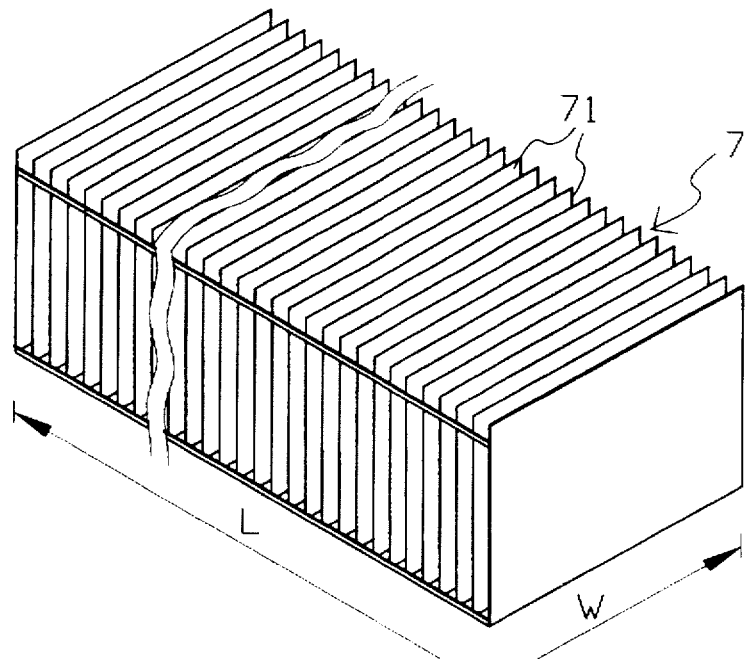
FIG. 3 shows a flat plate substrate assembly used in the preferred embodiment.

As shown in FIGS. 1, 2 and 3, a cultivating apparatus comprises a container 1 which has a culture chamber 11 for receiving a culture medium, upper and lower inlet ports 12 and 13 for feeding the culture medium, an outlet port 14 for discharging the culture medium, and an overflow port 15 to allow the outgoing of the overflow. A first storage tank 2 is provided at a level lower than the culture chamber 11 and a second storage tank 3 is provided at a level higher than the culture chamber 11.

4

A substrate means 7 including a plurality of substrate plates 71 is mounted in the culture chamber 11 to provide anchorage surfaces for cell growth. The substrate plates 71 are flat plates which extend vertically and spaced horizontally. Although only flat plates are shown as a cell anchorage substrate in this embodiment, the substrate means used in the present invention should not be limited thereto. Other substrates such as grid-like plates or packing materials which are used conventionally for attachment of cells, may also be used in the present invention.

A circulating system for circulating the culture medium comprises a feed pipe 41, a discharge pipe 42, an overflow pipe 43, while a recycling pipe line 44. The feed pipe 41 is connected to the inlet ports 12 and 13 and the second storage tank 3, and the discharge pipe 42 is connected to the outlet port 14 and the first storage tank 2. The overflow pipe 43 extends between the overflow port 15 and the first storage tank 2. The recycling pipe line 44 interconnects the first and second storage tanks 2 and 3 and incorporates a pump 45 which transports the culture medium from the first storage tank 2 to the second storage tank 3.

Valves v1, v2, v3, and v31 are provided to control the flow of the culture medium in the overflow pipe 43, the discharge pipe 42, and the inlet pipe 41. By means of the valve v31, which is a three-way valve, the culture medium may be fed into the culture chamber 11 through the upper or lower inlet ports 12 and 13 according to the requirements of the operation of the cultivating apparatus. Air filters F1 and F2 are provided for the culture chamber 11, and air filters F3 and F4 are provided for tanks 2 and 3 respectively. An air pump 5 is connected to the air filter F1 to draw fresh air into the culture chamber 11 when desired. A level meter 8 is connected to the first storage tank 2 to detect the surface level of the medium in the first storage tank 2. When the medium level reaches a predetermined level, the pump 45 is actuated to transport the medium to the second storage tank 3.

A siphon tube 6 has one arm connected to the first storage tank and the other arm connected to the discharge pipe 42. The height of the siphon tube 6 is arranged such that the siphon tube 6 starts to suction the medium from the culture medium into the first storage tank when the surface level of the culture medium reaches a level higher than the height of the substrate plates 71, which is almost as high as the overflow port 15.

The cultivating apparatus of the preferred embodiment may further comprises means for uniformly distributing the culture medium either at the top or bottom side of the culture chamber, or at both. As embodied herein, the uniformly distributing means 8 is provided at the top of the culture chamber 11 for uniformly distributing the culture medium onto the flat substrate plates 71. The means 8 comprises distributing tubes 81 which are connected to the inlet port 13 and which have a plurality of discharge openings distributed at the top side of the culture chamber 11, and a perforated tray 82 for receiving the culture medium from the distributing tubes 81 and for distributing the same onto the substrate plates 71. On the other hand, spraying devices (not shown) may be used instead of the perforated tray 82 for spraying the culture medium.

The operation of the apparatus begins from the stage of cell attachment. At this stage, a culture medium is fed into the culture chamber 11 from the second storage tank 3 by gravity or a gradient pressure at an appropriate constant rate controlled via valve v3. Valve v1 at the overflow port 15 is opened at the same time to maintain the surface level of the culture medium at a height h4 or a full surface level so as to submerge all the substrate plates 71 in the culture medium. The culture medium from the overflow port 15 flows down the first storage tank 2 through pipe 43 by gravity or gradient pressure. By virtue of the level meter 8 which monitors the medium level in the first storage tank 2, the pump 45 is controlled actuated to transport the culture medium to the second storage tank 3. When the medium level in the first storage tank 2 is below its lower limit, the pump 45 does not operate. As such, the culture medium is circulated through a looped path passing through the culture chamber 11, and the first and second storage tanks 2 and 3. The period of the circulation may be 30 minutes or may be shorter or longer depending on the duration required for cells to attach on the substrate.

After cells attach to the surfaces of the substrate plates 71, valve v1 is closed, and valve v2 is opened while valve v3 is still in its open situation. Since the surface level of the culture medium at this situation is at a full level or higher than the height of the siphon tube 6, the culture medium is drawn to the first storage tank 2 through the discharge port 14 by virtue of a suction created in the siphon tube 6. As the surface level is lowered, the anchorage surfaces of the substrate plates 71 are exposed and only a thin film of the medium is left on each substrate plate 71. The operation is repeated so that the substrate plates 71 are intermittently exposed from the culture medium. The operation is stopped when cells cover the surfaces of the substrate plates 71. The period of one cycle operation is preferably 30 seconds. Based on the constant volumetric flow rates f1 and f2 in pipes 41 and 43, the period of the cycle from the commencement of level descent to the end of level ascent may be determined as hereinafter described.

Referring to FIG. 2, h1 and h2 respectively represent the height of the bottom of the substrate plates 71 from the bottom of the culture chamber 11 and the height of the top of the substrate plates 71 from the bottom of the culture chamber 11. h3 is the height of the siphon tube 6 from the bottom of the culture chamber 11, and h4 is the height of overflow port from the bottom of the culture chamber 11. The height of the medium surface level is $h_t$. In FIG. 3, w is the width of the culture chamber, and 1 is the length thereof. When the culture medium is fed into the culture chamber to raise the medium surface level, the siphon tube 6 does not operate and the medium flow rate f2 (by volume) which is kept constant in pipe 43 is zero. In this situation, when $0<h_t<h1$, or $h2<h_t<h3$, the ascending rate of the surface level is given by the equation:

$$u1 = f1/wl \qquad (1)$$

When $h1 < h_t < h2$, the ascending rate of the surface level is given by the equation:

$$u1 = f1/w(l-Nd) \qquad (2)$$

(where N is the number of substrate plates and d is the thickness of each plate).

For the stage in which the medium surface level descends due to the operation of the siphon tube 6, assume that the medium flow rates f1 and f2 in pipes 41 and 43 are constant. In these circumstances, when $0<h_t<h1$ or $h2 <h_t<h3$, the descending rate of the surface level is given by the equation:

$$u_2 = \frac{f2-f1}{wl} \qquad (3)$$

When $h1<h_t<h2$, the descending rate of the surface level is given by the equation:

$$u_2 = \frac{f2-f1}{w(l-Nd)} \qquad (4)$$

Therefore, the time required to raise the medium surface level from 0 to h3 is given by the equation:

$$t_1 = w[(h1+h2+h3)l+(h2-h1)(l-Nd)]/f1 \qquad (5)$$

and the time required to lower the medium surface level from h3 to 0 is given by the equation:

$$t_2 = w[(h1+h3-h2)l+(h2-h1)(l-Nd)]/(f2-f1) \qquad (6)$$

As a result, the total time of the cycle from the commencement of level descent to the end of level ascent is:

$$t_p = t_1 + t_2 \qquad (7)$$

Although the preferred embodiment as described comprises stationary substrate plates which are intermittently exposed from the surface of the culture medium by raising and lowering the medium surface level, arrangements for moving upward and downward substrate plates may be used so as to expose and submerge the substrate plates.

While the present invention has been described in connection with what is considered the most practical and preferred embodiment, it is understood that this invention is not limited to the disclosed embodiment but is intended to cover various arrangements included within the spirit and scope of the broadest interpretations and equivalent arrangements.

We claim:

1. An apparatus for cultivating cells comprising:

a cell culture chamber having inlet and outlet means;

substrate means mounted inside said cell culture chamber for holding cells;

means for circulating a culture medium from said outlet means to said culture chamber through said inlet means, said circulating means being connected to said inlet and outlet means and operative to alternately raise and lower the level of the culture medium relative to said substrate means between a high level to submerge cells held by said substrate means in the culture medium and a low level to expose cells held by said substrate means to a gaseous environment present above the level of the culture medium, said circulating means being capable of causing the culture medium to flow in through said inlet means depending on the arrival of the culture medium level at said low level and causing the culture medium to flow out through said outlet means depending on the arrival of the culture medium level at said high level.

2. An apparatus as claimed in claim 1, wherein said circulating means comprises a first storage tank which is communicated with said outlet means and which is located at a level lower than the bottom of said cell culture chamber.

3. An apparatus as claimed in claim 2, wherein said circulating means further comprises a second storage tank which is communicated with said inlet means and is located downstream of said first storage tank, upstream of said culture chamber, and at a level higher than the top of said cell culture chamber.

4. An apparatus as claimed in claim 3, wherein said circulating means further comprises a pump means located between said first and second storage tanks and capable of providing fluid flow from said first storage tank to said second storage tank.

5. An apparatus as claimed in claim 4, wherein said circulating means further comprises a siphon device connected to said outlet means and said first storage tank, said siphon device creating a suction force when the surface level of said culture medium reaches a predetermined height in said cell culture chamber.

6. An apparatus as claimed in claim 4, wherein said circulating means further comprises a first control valve connected to said outlet for controlling the outflow of said culture medium, and a second control valve connected to said inlet means for controlling the flow of said culture medium into said cell culture chamber.

7. An apparatus as claimed in claim 2, wherein said circulating means further comprises an overflow tube communicated with said cell culture chamber at a level above the top of said substrate means, and an overflow valve connected to said overflow tube.

8. An apparatus as claimed in claim 4, wherein said circulating means further comprises means for detecting the surface level of said culture medium in said first storage tank and for actuating the operation of said pump.

9. An apparatus as claimed in claim 4, wherein said inlet means comprises a first inlet to said cell culture chamber at a level above the top of said substrate means, and a second inlet to said cell culture chamber at a level below the bottom of said substrate means.

10. An apparatus as claimed in claim 9, further comprising means for uniformly distributing the culture medium into said cell culture chamber, said distributing means being provided in said cell culture chamber above or below said substrate means.

11. An apparatus as claimed in claim 10, wherein said means for uniformly distributing the culture medium comprises means for spraying the culture medium provided above said substrate means.

12. An apparatus as claimed in claim 2, further comprising means for supplying gas into said cell culture chamber from the top of said cell culture chamber and means for releasing said gas from said cell culture chamber.

13. An apparatus as claimed in claim 3, further comprising means for removing metabolic waste from said culture medium, provided at at least one of said first and second storage tanks.

14. An apparatus as claimed in claim 3, further comprising means for supplying fresh culture medium into at least one of said first and second storage tanks.

15. A method for cultivating cells comprising:
  (a) providing a cell culture chamber with an inlet means, an outlet means, and substrate means;
  (b) feeding a culture medium containing cells into said cell culture chamber and allowing cells to attach to said substrate means;
  (c) circulating the culture medium from said outlet means to said culture chamber through said inlet means and alternately raising and lowering the level of the culture medium during cell growth between a high level to submerge cells held by said substrate means in the culture medium and a low level to expose cells held by said substrate means to a gaseous environment;
  (d) controlling the outflow of the culture medium through said outlet means depending upon the arrival of the culture medium at said high level; and
  (e) controlling the inflow of the culture medium through said inlet means depending upon the arrival of the culture medium at said low level.

* * * * *